United States Patent
Katayose

(10) Patent No.: US 8,604,444 B2
(45) Date of Patent: Dec. 10, 2013

(54) PARTICLE BEAM IRRADIATION APPARATUS AND PARTICLE BEAM THERAPY SYSTEM

(75) Inventor: Tadashi Katayose, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/702,419

(22) PCT Filed: Aug. 20, 2010

(86) PCT No.: PCT/JP2010/064073
§ 371 (c)(1),
(2), (4) Date: Dec. 6, 2012

(87) PCT Pub. No.: WO2012/023205
PCT Pub. Date: Feb. 23, 2012

(65) Prior Publication Data
US 2013/0075622 A1    Mar. 28, 2013

(51) Int. Cl.
*H01J 3/26* (2006.01)
(52) U.S. Cl.
CPC .................................. *H01J 3/26* (2013.01)
USPC .................................. 250/396 R; 250/492.3
(58) Field of Classification Search
USPC ........................................ 250/396 R, 492.3
See application file for complete search history.

(56) References Cited

U.S. PATENT DOCUMENTS

| | | | |
|---|---|---|---|
| 6,246,066 B1 * | 6/2001 | Yuehu | 250/492.3 |
| 8,222,613 B2 * | 7/2012 | Tajiri et al. | 250/398 |
| 8,232,536 B2 * | 7/2012 | Harada | 250/493.1 |
| 2004/0000650 A1 | 1/2004 | Yanagisawa et al. | |
| 2011/0218429 A1 | 9/2011 | Harada et al. | |

FOREIGN PATENT DOCUMENTS

| | | |
|---|---|---|
| JP | 8-257148 A | 10/1996 |
| JP | 10-332896 A | 12/1998 |
| JP | 2004-321830 A | 11/2004 |
| JP | 4393581 B1 | 1/2010 |
| JP | 2010-029594 A | 2/2010 |

OTHER PUBLICATIONS

International Search Report (PCT/ISA/210) issued on Oct. 5, 2010, by the Japanese Patent Office as the International Searching Authority for International Application No. PCT/JP2010/064073.

* cited by examiner

*Primary Examiner* — Kiet T Nguyen
(74) *Attorney, Agent, or Firm* — Buchanan Ingersoll & Rooney PC

(57) ABSTRACT

The particle beam irradiation apparatus irradiates a charged particle beam accelerated by a accelerator onto an irradiation subject; the particle beam irradiation apparatus includes a scanning electromagnet that scans the charged particle beam, and a scanning electromagnet moving apparatus that moves the scanning electromagnet in such a way as to change the distance between the scanning electromagnet and the irradiation subject in the beam axis direction of the charged particle beam.

20 Claims, 8 Drawing Sheets

FIG. 3
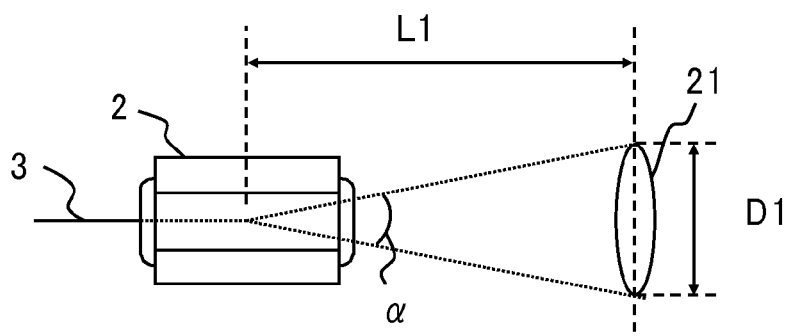
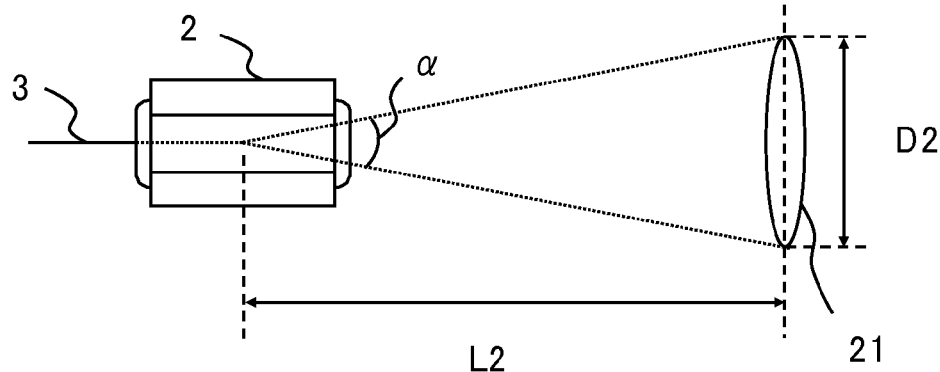
FIG. 4
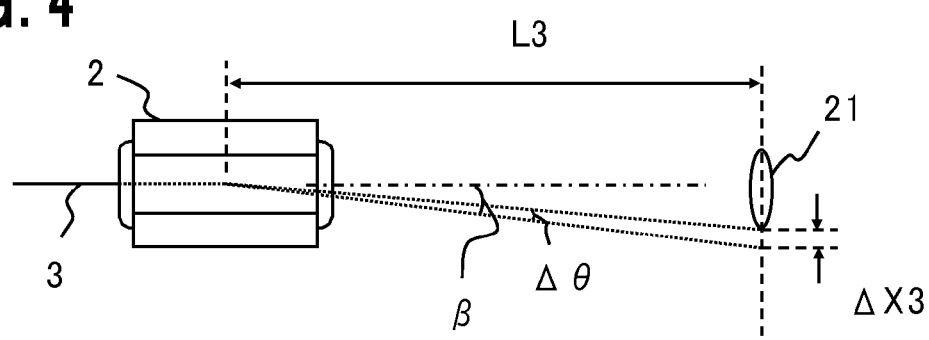
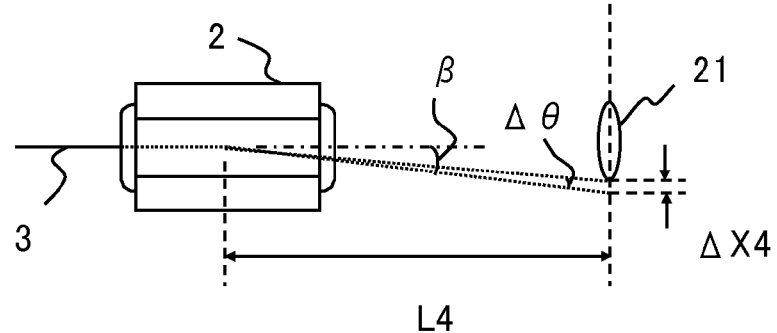

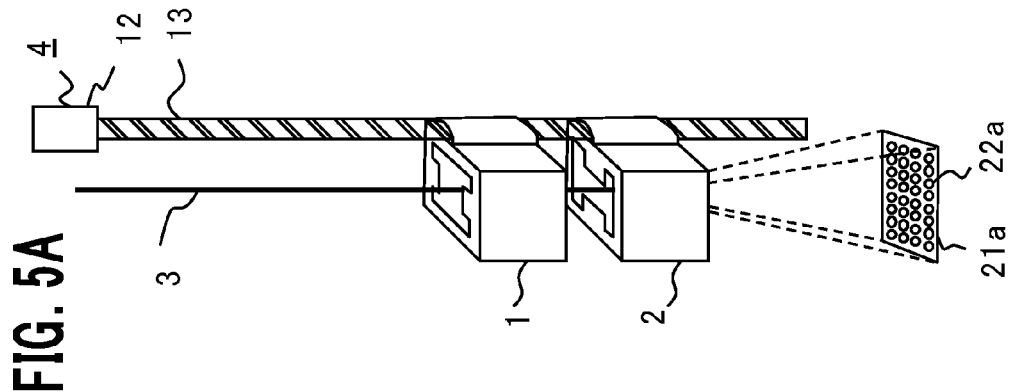
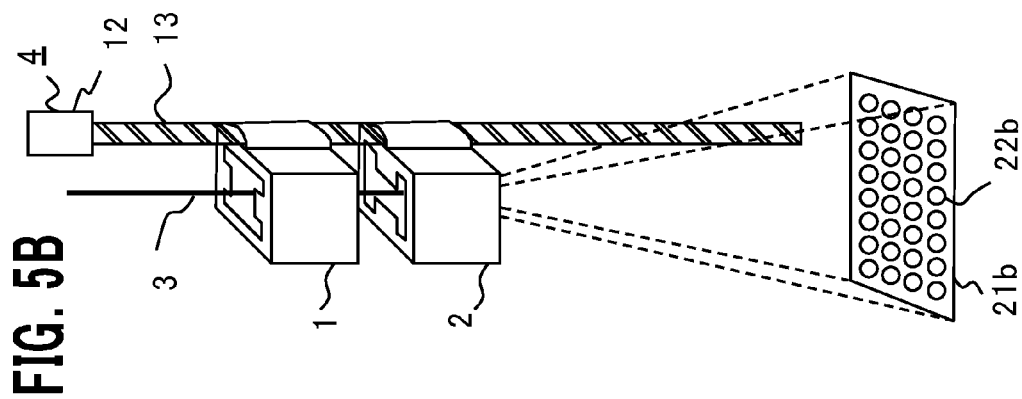
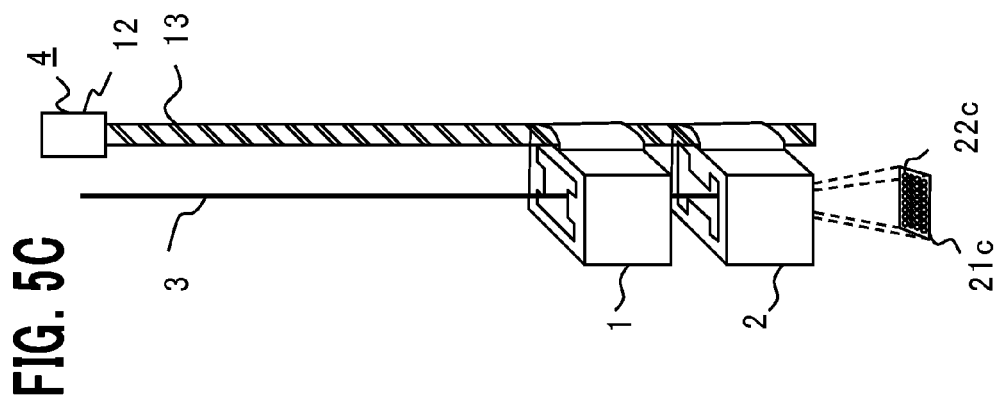

PARTICLE BEAM IRRADIATION APPARATUS AND PARTICLE BEAM THERAPY SYSTEM

TECHNICAL FIELD

The present invention relates to a particle beam irradiation apparatus and a particle beam therapy system for performing treatment of a cancer or the like by use of a particle beam.

BACKGROUND ART

In general, a particle beam therapy system is provided with a beam generation apparatus that generates a charged particle beam, an accelerator that is connected with the beam generation apparatus and accelerates a generated charged particle beam, a beam transport system that transports a charged particle beam that is accelerated by the accelerator so as to gain predetermined energy and then emitted, and a particle beam irradiation apparatus, disposed at the downstream side of the beam transport system, for irradiating a charged particle beam onto an irradiation subject. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

The size of a beam transported from an accelerator is several millimeters, in general; in contrast, in the case of medicine, the irradiation coverage of a charged particle beam needs to be several tens of centimeters square or larger. In order to obtain a wide irradiation field by use of a thin charged particle beam, the foregoing scanning irradiation method is utilized.

Patent Document 1 discloses the following invention whose objective is to provide a rotating gantry that enlarges the irradiation coverage in a direction that is parallel to the deflection plane, while keeping the intensity of the scanning electromagnet as large as the intensity of a conventional one. In the invention disclosed in Patent Document 1, the deflection electromagnet and the irradiation field moving electromagnet at the upstream side of the scanning electromagnet change the downstream beam position; the scanning electromagnet is moved to the beam positions a and b; an irradiatable area A is irradiated and, after that, the charged particle beam is made to pass through the other position b at the downstream side of the deflection electromagnet; then, the scanning electromagnet is moved to the beam position b and an area B is irradiated; in such a manner, the irradiation coverage is enlarged in each of the areas A and B.

PRIOR ART REFERENCE

Patent Document

[Patent Document 1] Japanese Patent Application Laid-Open No. H8-257148

DISCLOSURE OF THE INVENTION

Problem(s) to be Solved by the Invention

The irradiation coverage (irradiation field) and the irradiation position accuracy differ in various manners, depending on the shape of a diseased site; in the case where the irradiation coverage is narrow, a high irradiation position accuracy is required, and in the case where the irradiation coverage is wide, a lower irradiation position accuracy may be required. In the spot scanning irradiation method, in general, in the case where the irradiation coverage is narrow and a high irradiation position accuracy is required, a small-size charged particle beam is irradiated at small spacing (spot spacing), and in the case where the irradiation coverage is wide and a lower irradiation position accuracy is required, a large-size charged particle beam is irradiated at large spacing (spot spacing).

The maximum irradiation coverage formed of a charged particle beam is determined by the swing angle, of the scanning electromagnet, that is achieved by the maximum current of the excitation power source for the scanning electromagnet; thus, in the irradiation method, disclosed in Patent Document 1, utilizing a rotating gantry, each of the respective maximum irradiation coverage areas in the areas A and B is determined by the distance between the scanning electromagnet and the irradiation position. The maximum position accuracy of a charged particle beam in the irradiation coverage is determined by the minimum controllable swing angle that is achieved by the minimum controllable current of the excitation power source; thus, in the irradiation method, disclosed in Patent Document 1, utilizing a rotating gantry, each of the respective maximum position accuracies in the areas A and B is determined by the distance between the scanning electromagnet and the irradiation position.

In the irradiation method, disclosed in Patent Document 1, utilizing a rotating gantry, by changing excitation currents of the deflection electromagnet and the irradiation field moving electromagnet at the upstream side of the scanning electromagnet, and by moving the scanning electromagnet, the irradiation coverage (irradiation field) can be enlarged. However, it is required to utilize the deflection electromagnet and the irradiation field moving electromagnet at the upstream side of the scanning electromagnet. Moreover, because in the irradiation method, disclosed in Patent Document 1, utilizing a rotating gantry, the distance between the scanning electromagnet and the irradiation position is constant, the minimum controllable swing angle is constant, whereby the irradiation position accuracy cannot be raised. Accordingly, there has been a problem that it is not made possible to perform diverse-variation irradiation in which irradiation fields and irradiation position accuracies are combined.

The present invention has been implemented in order to solve the foregoing problems; the objective thereof is to obtain a particle beam irradiation apparatus that can perform in a changeable manner the combination of a plurality of parameters in particle beam irradiation, such as the combination of irradiation fields and irradiation position accuracies, and that can perform diverse-variation irradiation.

Means for Solving the Problems

A particle beam irradiation apparatus that irradiates a charged particle beam accelerated by an accelerator onto an irradiation subject, the particle beam irradiation apparatus includes a scanning electromagnet that scans the charged particle beam and a scanning electromagnet moving apparatus that moves the scanning electromagnet in such a way as to change the distance between the scanning electromagnet and the irradiation subject in the beam axis direction of the charged particle beam.

Advantage of the Invention

Because a particle beam irradiation apparatus according to the present invention changes the distance between an irradiation subject and a scanning electromagnet in the beam axis direction of a charged particle beam, it is made possible to perform the combination of a plurality of parameters in particle beam irradiation, such as the combination of irradiation fields and irradiation position accuracies; thus, diverse-variation irradiation can be implemented.

BRIEF DESCRIPTION OF THE DRAWINGS

FIG. 3 is a set of diagrams illustrating the relationship between axis-direction movement of the scanning electromagnet in FIG. 2 and the area of an irradiation field;

FIG. 4 is a set of diagrams illustrating the relationship between axis-direction movement of the scanning electromagnet in FIG. 2 and an irradiation position error;

FIG. 5A, FIG. 5B and FIG. 5C are views for explaining irradiation by a particle beam irradiation apparatus according to Embodiment 1;

BEST MODE FOR CARRYING OUT THE INVENTION

Embodiment 1

Figure 1:
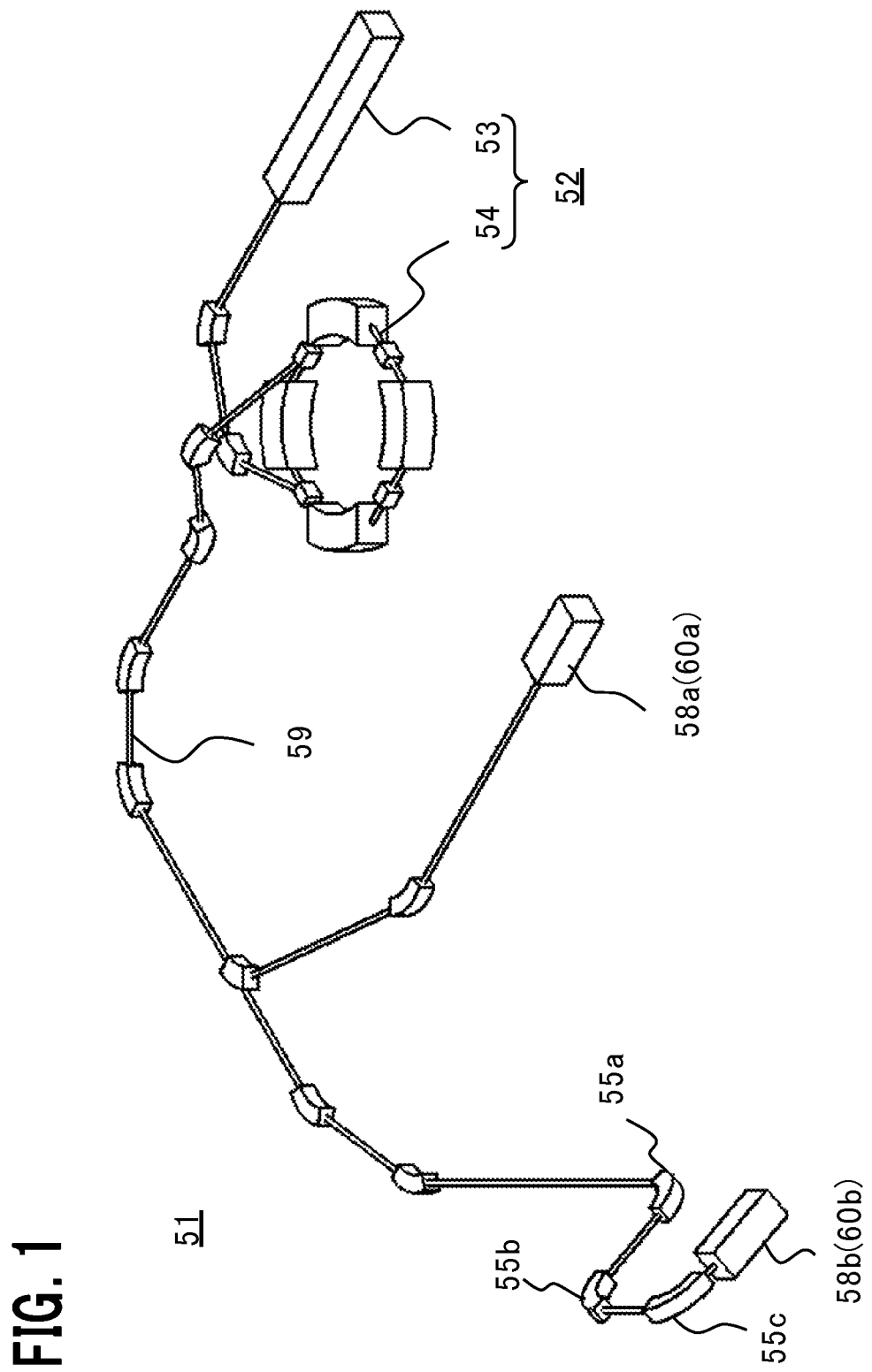
FIG. 1 is a schematic configuration diagram of a particle beam therapy system according to the present invention.

FIG. 1 is a schematic configuration diagram of a particle beam therapy system according to the present invention. A particle beam therapy system 51 includes a beam generation apparatus 52, a beam transport system 59, and particle beam irradiation apparatuses 58a and 58b (or 60a and 60b). The beam generation apparatus 52 includes an ion source (unillustrated), a prestage accelerator 53, and a synchrotron 54. The particle beam irradiation apparatus 58b (60b) is provided in a rotating gantry (unillustrated). The particle beam irradiation apparatus 58a (60a) is provided in a treatment room where no rotating gantry is installed. The function of the beam transport system 59 is to achieve communication between the synchrotron 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam 3, which is a particle beam such as a proton beam generated in ion source, is accelerated by the prestage accelerator 53 and enters the synchrotron 54. The particle beam 3 is accelerated to obtain predetermined energy. The charged particle beam 3 launched from the synchrotron 54 is transported to the particle beam irradiation apparatuses 58a (60a) and 58b (60b) by way of the beam transport system 59. The particle beam irradiation apparatuses 58a (60a) and 58b (60b) each irradiate the charged particle beam 3 onto an irradiation subject 11 (refer to FIG. 2).

Figure 2:
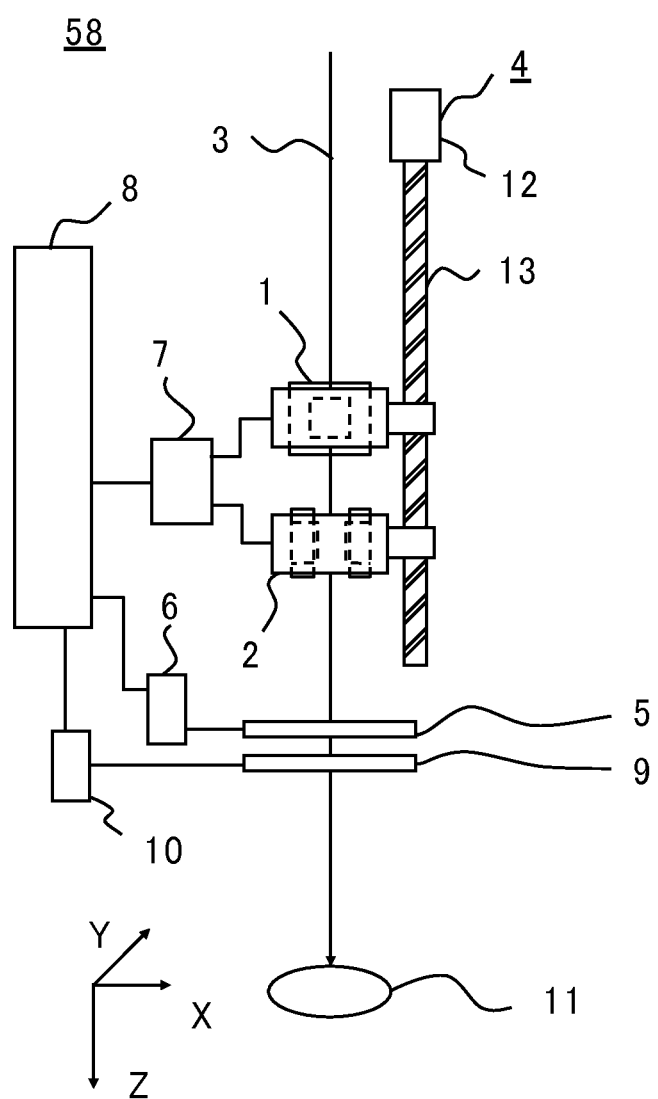
FIG. 2 is a configuration diagram illustrating a particle beam irradiation apparatus according to Embodiment 1 of the present invention.

FIG. 2 is a configuration diagram illustrating a particle beam irradiation apparatus according to Embodiment 1 of the present invention. A charged particle beam 3 generated in the beam generation apparatus 52 and accelerated to gain predetermined energy is led to the particle beam irradiation apparatus 58 by way of the beam transport system 59. The particle beam irradiation apparatus 58 is provided with X-direction and Y-direction scanning electromagnets 1 and 2 that scan the charged particle beam 3 in the X direction and the Y direction, respectively, which are directions perpendicular to the charged particle beam 3; a position monitor 9; a dose monitor 5; a scanning electromagnet power source 7; a scanning electromagnet moving apparatus 4 that moves the X-direction scanning electromagnet 1 and the Y-direction scanning electromagnet 2; a dose data converter 6; a position data converter 10; and an irradiation control apparatus 8 that controls the irradiation system of the particle beam irradiation apparatus 58. The scanning electromagnet moving apparatus 4 includes a motor 12 and a ball screw 13; the ball screw 13 rotated by the motor 12, moves the X-direction scanning electromagnet 1 and the Y-direction scanning electromagnet 2, by the intermediary of female screw mechanisms fixed to the X-direction scanning electromagnet 1 and the Y-direction scanning electromagnet 2. The X-direction scanning electromagnet 1, the Y-direction scanning electromagnet 2, the position monitor 9, and the dose monitor 5 configure an irradiation system. The traveling direction of the charged particle beam 3 is the Z direction.

The X-direction scanning electromagnet 1 and the Y-direction scanning electromagnet 2 scan the charged particle beam 3 in the X direction and the Y direction, respectively. The position monitor 9 detects a beam peak position (passing position) through which the charged particle beam 3 that has been scanned by the X-direction scanning electromagnet 1 and the Y-direction scanning electromagnet 2 passes. The dose monitor 5 detects the dose of the charged particle beam 3. The irradiation control apparatus 8 controls the irradiation position of the charged particle beam 3 on an irradiation subject 11, based on treatment plan data generated by an unillustrated treatment planning apparatus; when the dose measured by the dose monitor 5 and converted into digital data by the dose data converter 6 reaches the desired dose, the charged particle beam 3 is stopped. The scanning electromagnet power source 7 changes setting currents for the X-direction scanning electromagnet 1 and the Y-direction scanning electromagnet 2, based on control inputs (command currents), which are outputted from the irradiation control apparatus 8, to the X-direction scanning electromagnet 1 and the Y-direction scanning electromagnet 2.

Next, there will be explained the relationship between the axis-direction movement of a scanning electromagnet and the area of an irradiation field and the relationship between the axis-direction movement of a scanning electromagnet and an irradiation position error. FIG. 3 is a set of diagrams illustrating the relationship between axis-direction movement of the scanning electromagnet and the area of an irradiation field. In the scanning irradiation method, an irradiation field is formed by two-dimensionally scanning the charged particle beam 3 on one of a plurality of layers (slices) into which the irradiation subject 11 is divided. The irradiation field changes depending on the beam-axis-direction distance between the scanning electromagnet and one layer, of the irradiation subject 11, that is an irradiation position. FIG. 3(a) illustrates a case where the distance between one slice and the Y-direction scanning electromagnet 2 is L1; FIG. 3(b) illustrates a case where the distance between the foregoing slice and the Y-direction scanning electromagnet 2 is L2. FIG. 3 illustrates a case where L1<L2. Here, each of L1 and L2 denotes the distance between the slice and the center of the magnetic pole of the scanning electromagnet 2 that scans the charged particle beam 3. In FIG. 3(a), in the case where the charged particle beam 3 is scanned at the maximum swing angle α, the scanning range length, which is the end-to-end length of a Y-direction scanning range 21, becomes D1. Similarly, in FIG. 3(b), in the case where the charged particle beam 3 is scanned at the maximum swing angle α, the scanning range length, which is the end-to-end length of the Y-direction scanning range 21, becomes D2.

The scanning range lengths D1 and D2 are expressed by the equations (1) and (2), respectively.

$$D1 = 2 \times L1 \times \tan \alpha \quad (1)$$

$$D2 = 2 \times L2 \times \tan \alpha \quad (2)$$

Because the distance L1<the distance L2, the scanning range length D1<the scanning range length D2. Accordingly, in the case where the beam-axis-direction distance between the scanning electromagnet and the irradiation position (one of the layers of the irradiation subject 11) is large, the scanning range 21 can be widened and the scanning range length can be lengthened. In the case where the beam-axis-direction distance between the scanning electromagnet and the irradiation position is small, the scanning range 21 can be narrowed and the scanning range length can be shortened.

The relationship between axis-direction movement of a scanning electromagnet and an irradiation position error will be explained with reference to FIG. 4. When an organ, for which radiation or the charged particle beam 3 is a high risk, is in the vicinity of an irradiation position, the irradiation position accuracy is important. FIG. 4 is a set of diagrams illustrating the relationship between axis-direction movement of the scanning electromagnet and an irradiation position error. The irradiation position error is a movement width determined by the position accuracy of the charged particle beam 3 in an irradiation position and changes depending on the beam-axis-direction distance between the scanning electromagnet and one layer, of the irradiation subject 11, that is the irradiation position. The positional accuracy of the charged particle beam 3 is determined by the generated magnetic field accuracies of the X-direction scanning electromagnet 1 and the Y-direction scanning electromagnet 2. Depending on the generated magnetic field accuracy of the scanning electromagnets 1 and 2, the charged particle beam 3 changes within the accuracy $\Delta\theta$ of the swing angle, with respect to a given desired irradiation position (desired swing angle). FIG. 4(a) illustrates a case where the distance between one slice and the Y-direction scanning electromagnet 2 is L3; FIG. 4(b) illustrates a case where the distance between the foregoing slice and the Y-direction scanning electromagnet 2 is L4. FIG. 4 illustrates a case where L4<L3. Here, each of L3 and L4 denotes the distance between the slice and the center of the magnetic pole of the scanning electromagnet 2 that scans the charged particle beam 3. In FIG. 4(a), in the case where the accuracy of the swing angle of the charged particle beam 3 is $\Delta\theta$, the irradiation position error becomes $\Delta X3$. Similarly, in FIG. 4(b), in the case where the accuracy of the swing angle of the charged particle beam 3 is $\Delta\theta$, the irradiation position error becomes $\Delta X4$.

When the accuracy of the swing angle is $\Delta\theta$, the irradiation position errors $\Delta X3$ and $\Delta X4$ at a time when the swing angles are $\beta$ and $\beta-\Delta\theta$, for example, are expressed by the equations (3) and (4), respectively.

$$\Delta X3 = L3 \times A \quad (3)$$

$$\Delta X4 = L4 \times A \quad (4)$$

where $A = \tan \beta - \tan(\beta - \Delta\theta)$.

Because the distance L4<the distance L3, the irradiation position error $\Delta X4$<the irradiation position error $\Delta X3$. Accordingly, in the case where the beam-axis-direction distance between the scanning electromagnet and the irradiation position (one of the layers of the irradiation subject 11) is large, the irradiation position error becomes large and the irradiation position accuracy is deteriorated. In contrast, in the case where the beam-axis-direction distance between the scanning electromagnet and the irradiation position is small, the irradiation position error can be reduced and the irradiation position accuracy can be raised.

In general, when the size of the irradiation spot (referred to simply as a spot, hereinafter) at an irradiation position of the charged particle beam 3 is small, irradiation of the irradiation subject 11 is implemented at small spacing (spot spacing) so that the irradiation subject 11 is irradiated without any space and with a predetermined dose; therefore, the irradiation position error restriction for each spot is strict. Here, an irradiation spot is an irradiation unit into which the irradiation subject is divided for the purpose of controlling the irradiation dose. For example, it is assumed that when the spot diameter is 5 mm, the irradiation position error restriction is the same as or smaller than 0.5 mm (10%). Provided the beam-axis-direction distance between the irradiation position and the scanning electromagnet is 5 m and the irradiation position error is 1 mm, the irradiation position error restriction of under 0.5 mm at a time when the spot diameter is 5 mm cannot be achieved; however, by setting the distance to be the same as or smaller than 2.5 mm, the irradiation position error restriction of under 0.5 mm can be achieved.

In general, in the case where the demand for the irradiation position accuracy is not strict, the charged particle beam 3 having a large spot size is irradiated at large spacing (spot spacing). In this case, the beam-axis-direction distance between the irradiation position and the scanning electromagnet is set to be long. As described above, in the case where the beam-axis-direction distance between the irradiation position and the scanning electromagnet is long, the scanning range 21 can be widened and the scanning range length can be lengthened. Therefore, by setting the beam-axis-direction distance between the irradiation position and the scanning electromagnet to be long, the spot size can be enlarged and a wide irradiation field can be formed.

In the particle beam irradiation apparatus 58 according to embodiment 1, the scanning electromagnet moving apparatus 4 changes the distance between the X-direction scanning electromagnet 1/the Y-direction scanning electromagnet 2 and the irradiation subject 11, so that the maximum irradiation field and the irradiation position accuracy suitable for the irradiation subject 11 can be selected. FIG. 5A, FIG. 5B and FIG. 5C are views for explaining irradiation by a particle beam irradiation apparatus according to Embodiment 1. FIGS. 5A through 5C illustrate three cases where the respective distances between the X-direction scanning electromagnet 1/the Y-direction scanning electromagnet 2 and the irradiation subject 11 are different from one another; FIG. 5A is a case where the distance is intermediate; FIG. 5B is a case where the distance is longer than that in FIG. 5A; FIG. 5C is a case where the distance is shorter than that in FIG. 5A. In FIGS. 5A through 5C, Reference Characters 21a, 21b and 21c denote the respective maximum scanning ranges in the foregoing three cases; Reference Characters 22a, 22b, and 22c denote the respective beam spots in the foregoing three cases.

In the case where the irradiation subject 11 is large and hence the maximum irradiation field needs to be enlarged, the X-direction scanning electromagnet 1 and the Y-direction scanning electromagnet 2 are moved, in the beam axis direction of the charged particle beam 3, by the scanning electromagnet moving apparatus 4, as illustrated in FIG. 5B, in the direction in which the X-direction scanning electromagnet 1 and the Y-direction scanning electromagnet 2 depart from the irradiation subject 11. In the case where the irradiation subject 11 is small or even large and the irradiation position error needs to be reduced, the X-direction scanning electromagnet 1 and the Y-direction scanning electromagnet 2 are moved, in the beam axis direction of the charged particle beam 3, by the scanning electromagnet moving apparatus 4, as illustrated in FIG. 5C, in the direction in which the X-direction scanning electromagnet 1 and the Y-direction scanning electromagnet 2 head for the irradiation subject 11, and up to the position where a predetermined irradiation position accuracy is achieved.

The irradiation control apparatus 8 generates control inputs (command currents) for the X-direction scanning electromagnet 1 and the Y-direction scanning electromagnet 2, based on the irradiation position accuracy and the desired position coordinates in treatment plan data generated by the treatment planning apparatus. In order to deal with predetermined irradiation position accuracies, the irradiation control apparatus 8 has a plurality of conversion tables and command value generation polynomials. The conversion table and the command value generation polynomial are control input generation units that generate control inputs. Here, the method in which the conversion table is utilized will be referred to as a conversion table method, and the method in which the command value generation polynomial is utilized will be referred to as a polynomial method.

The conversion table method will be explained. The conversion table is a table in which control inputs and irradiation position coordinates are tabularized, base on actual data on control inputs obtained through actual irradiation and measured irradiation position coordinates. Setting current values for the X-direction scanning electromagnet 1 and the Y-direction scanning electromagnet 2 are calculated by use of this conversion table, based on the desired position coordinates of the charged particle beam 3. The control input to be transmitted to the scanning electromagnet power source 7 is a control input (command) for making the scanning electromagnet power source 7 output the calculated setting current values. As far as the conversion table is concerned, two or more conversion tables having different irradiation position accuracies are prepared. In other words, two or more conversion tables are prepared for respective representative position accuracies. The irradiation control apparatus 8 generates control inputs in such a way that when there exists a conversion table that coincides with the designated irradiation position accuracy, that conversion table is utilized and when there exists no conversion table that coincides with the designated irradiation position accuracy, data of the immediately-prior conversion table or the immediately-post conversion table is supplemented (linear supplement or the like).

The polynomial method will be explained. The command value generation polynomial is the relationship, between the control input and the desired position coordinates of the charged particle beam 3, that is expressed by a polynomial obtained by modifying, based on the one-to one relationship between the excitation current and the magnetic field, polynomials for the measurement values of the magnetic fields of the X-direction scanning electromagnet 1 and the Y-direction scanning electromagnet 2 and the irradiation position coordinates at a time when irradiation is actually implemented. For example, letting Pt=(xt, yt) denote the desired irradiation position coordinates, the control input Ic (Ix, Iy) is expressed by the equations (5) and (6).

$$Ix = m_0 + m_1 xt + m_2 xt^2 + m_3 yt + m_4 xtyt + m_5 yt^2 \tag{5}$$

$$Iy = n_0 + n_1 xt + n_2 xt^2 + n_3 yt + n_4 xtyt + n_5 yt^2 \tag{6}$$

where $m_0$ through $m_5$ and $n_0$ through $n_5$ are parameter constants obtained through the least square method or the like. This polynomial method makes it possible to take the interference term such as xtyt into consideration and hence can generate the control input Ic having an accuracy higher than the accuracy of the control input generated through the conversion table method. Accordingly, by utilizing the polynomial method, the irradiation position accuracy, which depends on the distance between the irradiation position and the scanning electromagnet, can further be raised.

Also in the polynomial method, for each irradiation position accuracy, which depends on the distance between the irradiation position and the scanning electromagnet, two or more command value generation polynomials are prepared. Each of the selected irradiation position accuracies is a representative position accuracy. The irradiation control apparatus 8 generates control inputs in such a way that when there exists a command value generation polynomial that coincides with the designated irradiation position accuracy, that command value generation polynomial is utilized and when there exists no command value generation polynomial that coincides with the designated irradiation position accuracy, data generated from the immediately-prior command value generation polynomial or the immediately-post command value generation polynomial is supplemented (linear supplement or the like).

Figure 6:
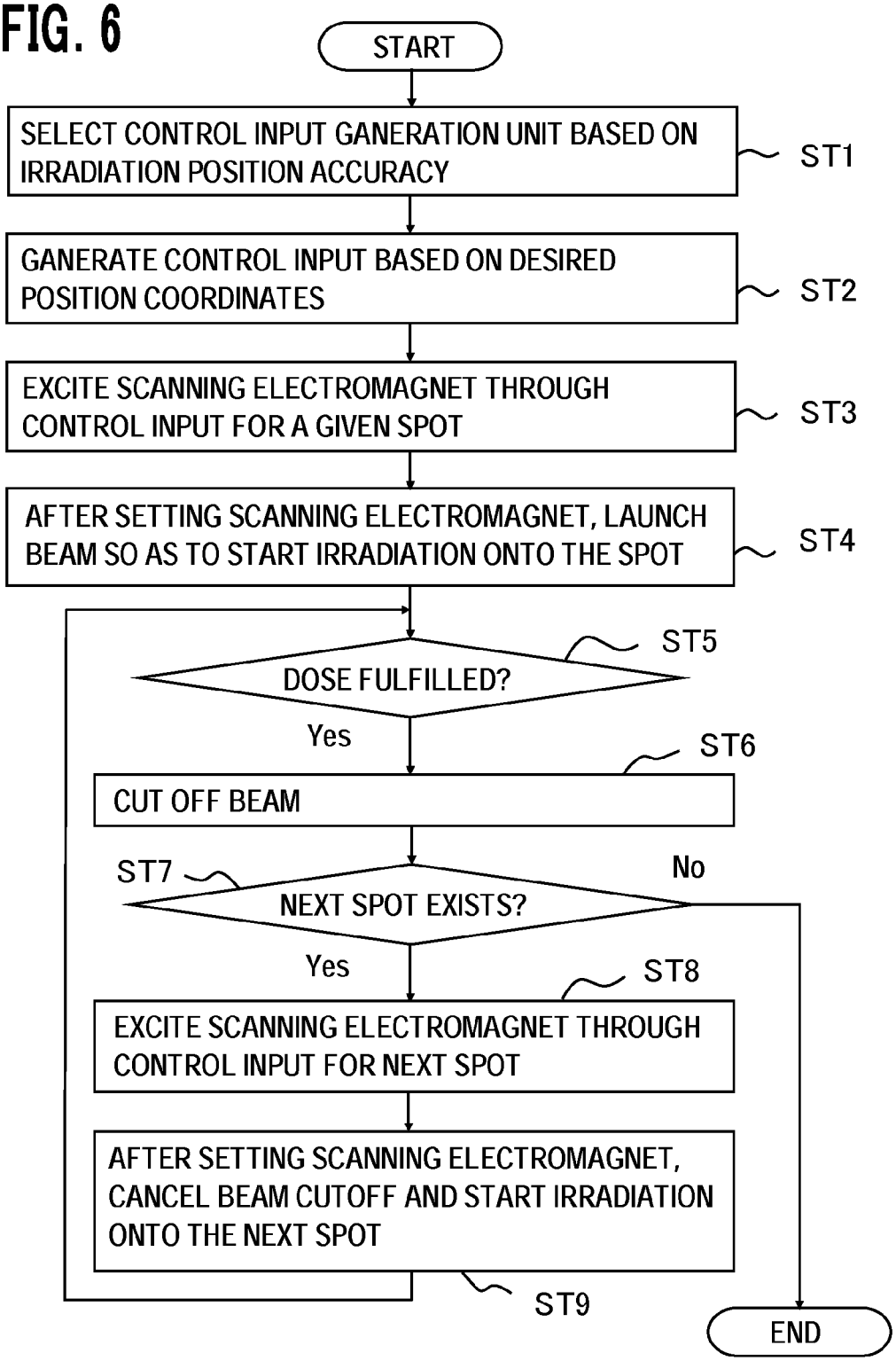
FIG. 6 is a flowchart representing a control method for a particle beam irradiation apparatus according to Embodiment 1.

The operation of the particle beam irradiation apparatus 58 will be explained with reference to the flowchart in FIG. 6. FIG. 6 is a flowchart representing a control method for a particle beam irradiation apparatus according to Embodiment 1. The particle beam irradiation apparatus 58 selects the to-be-used control input generation units such as a conversion table and a command value generation polynomial, based on the irradiation position accuracy in treatment plan data generated by the treatment planning apparatus (the step ST1: a control input generation unit selection procedure). Next, based on the desired position coordinates in the treatment plan data, the selected control input generation unit generates the control input Ic (Ix, Iy) (the step ST2: a control input generation procedure).

In the spot scanning method, with regard to a given spot on a site to be treated, the dose of the charged particle beam 3, determined by the treatment plan, is irradiated onto the irradiation subject 11; thus, at first, the scanning electromagnets 1 and 2 are excited through the control input for the given spot (the step ST3). Specifically, the irradiation control apparatus 8 sends control inputs corresponding to the position of the given spot to the scanning electromagnet power source 7; the scanning electromagnet power source 7 excites the scanning electromagnets 1 and 2 through the excitation currents designated by the control inputs for X-direction scanning electromagnet 1 and the Y-direction scanning electromagnet 2.

After the setting of the scanning electromagnets 1 and 2 has been completed, for example, in response to signals, from the X-direction scanning electromagnet 1 and the Y-direction scanning electromagnet 2, that indicate the completion of the setting, the charged particle beam 3 is launched into the particle beam irradiation apparatus 58, so that the irradiation onto the spot is started (the step ST4).

The irradiation control apparatus 8 determines whether or not irradiation onto the spot has been implemented as per the treatment plan, i.e., whether or not the irradiation dose detected by the dose monitor 5 has been fulfilled (whether or not the irradiation dose has reached the planned dose) (the step ST5). In the case where the irradiation dose has been fulfilled, the charged particle beam 3 is cut off (the step ST6).

The irradiation control apparatus 8 determines whether or not the next spot exists; in the case where the next spot exists, the step ST8 is implemented, and in the case where no next spot exists, the irradiation is ended (the step ST7). In the step ST8, the scanning electromagnets 1 and 2 are excited through the control inputs for the next spot. The operation is performed in the same manner as in the step ST3.

After the setting of the scanning electromagnets 1 and 2 has been completed, the cutoff of the charged particle beam 3 is cancelled; then, irradiation onto the spot is started (the step ST9). After the operation in the step ST9 has been completed, the step ST5 is resumed. The foregoing operation is repeated until irradiation onto all the spots on a single layer (slice) out of a plurality of layers in the irradiation subject 11 is completed. After the irradiation onto a single slice has been completed, the energy of the charged particle beam 3 is changed and the steps ST3 through ST9 are implemented so that irradiation onto another slice is performed.

In the particle beam irradiation apparatus 58 according to embodiment 1, the scanning electromagnet moving apparatus 4 changes the distance between the X-direction scanning electromagnet 1/the Y-direction scanning electromagnet 2 and the irradiation subject 11, so that the maximum irradiation field and the irradiation position accuracy suitable for the irradiation subject 11 can be selected. In the particle beam irradiation apparatus 58 according to Embodiment 1, the distance between the scanning electromagnet and the irradiation position is fixed almost constant; therefore, unlike conventional apparatuses in which the irradiation position accuracy at an irradiation position cannot freely be changed, the irradiation position accuracy can appropriately be changed in accordance with the irradiation subject 11. In addition, the combination of the irradiation field and the irradiation position accuracy can be changed, whereby diverse irradiation variations can be set.

In the particle beam irradiation apparatus 58 according to Embodiment 1, in the case where the irradiation position accuracy does not need to be raised so much but the maximum irradiation field needs to be enlarged, the scanning electromagnet moving apparatus 4 is moved while the irradiation position accuracy is kept within the allowable range, and there is generated the control input (command current) Ic for setting the excitation currents for the X-direction scanning electromagnet 1 and the Y-direction scanning electromagnet 2. In this case, because as illustrated in FIG. 5B, the beam spot 22b becomes large, the number of spots irradiated onto the irradiation subject 11 is smaller than that in the case where the beam spot is small; thus, the total irradiation time can be shortened.

In some cases, for the purpose of preventing the charged particle beam 3 from scattering in the air and the beam size from becoming large in a particle beam irradiation apparatus, the charged particle beam 3 is moved through the vacuum duct toward the vicinity of the irradiation subject 11. In this case, metal such as the flange of a vacuum duct is likely to exist in the space between the X-direction scanning electromagnet 1 and the Y-direction scanning electromagnet 2; therefore, in conventional particle beam irradiation apparatuses, heating in the metal, caused by the alternating magnetic field, is worried. However, in the particle beam irradiation apparatus 58 according to Embodiment 1, the beam-axis-direction space between the X-direction scanning electromagnet 1 and the Y-direction scanning electromagnet 2 can freely be changed; therefore, in the case of irradiation that generates a magnetic field causing concern about the heating, it is made possible to temporarily enlarge the space so as to prevent heating.

In general, a building in which a particle beam irradiation apparatus is installed is constructed with reinforced concrete; due to aged deterioration or an earthquake, the height of the floor or the ceiling may change. Therefore, it is required that the displacement is periodically measured and the position of the scanning electromagnet in the beam axis direction is corrected in order to maintain the distance between the scanning electromagnet and the irradiation position. In the particle beam irradiation apparatus 58 according to embodiment 1, the scanning electromagnet moving apparatus 4 makes it possible to perform the position correction easily.

There has been explained a case where the scanning electromagnet moving apparatus 4 is utilized commonly for the X-direction scanning electromagnet 1 and the Y-direction scanning electromagnet 2, i.e., the X-direction scanning electromagnet 1 and the Y-direction scanning electromagnet 2 are concurrently moved; however, it may be allowed that the X-direction scanning electromagnet 1 and the Y-direction scanning electromagnet 2 have their respective scanning electromagnet moving apparatuses 4. Not being limited to the configuration consisting of the motor 12 and the ball screw 13 illustrated in the drawings, an apparatus having an appropriate configuration can be adopted as the scanning electromagnet moving apparatus 4.

In the case where the configuration where the X-direction scanning electromagnet 1 and the Y-direction scanning electromagnet 2 are independently moved is adopted, the particle beam irradiation apparatus 58 is operated in the following manner: In the case where the irradiation subject 11 is large and hence the maximum irradiation field needs to be enlarged, at least one of the X-direction scanning electromagnet 1 and the Y-direction scanning electromagnet 2 is moved, in the beam axis direction of the charged particle beam 3, by the scanning electromagnet moving apparatus 4, as illustrated in FIG. 5B, in the direction in which the X-direction scanning electromagnet 1 and the Y-direction scanning electromagnet 2 depart from the irradiation subject 11. The maximum irradiation field is enlarged in the scanning direction of the scanning electromagnets that have been moved in the direction in which the scanning electromagnets depart from the irradiation subject 11. In the case where the irradiation subject 11 is small or even large and the irradiation position error needs to be reduced, at least one of the X-direction scanning electromagnet 1 and the Y-direction scanning electromagnet 2 is moved, in the beam axis direction of the charged particle beam 3, by the scanning electromagnet moving apparatus 4, as illustrated in FIG. 5C, in the direction in which the X-direction scanning electromagnet 1 and the Y-direction scanning electromagnet 2 head for the irradiation subject 11, and up to the position where a predetermined irradiation position accuracy is achieved. The irradiation position accuracy is raised in the scanning direction of the scanning electromagnets that have been moved in the direction in which the scanning electromagnets head for the irradiation subject 11.

As described above, the particle beam irradiation apparatus 58 according to Embodiment 1 is provided with the scanning electromagnets 1 and 2 and the scanning electromagnet moving apparatus 4 that moves the scanning electromagnets 1 and 2 in such a way as to change the distance, in the beam axis direction of the charged particle beam 3, between the scanning electromagnets 1 and 2 and the irradiation subject 11; therefore, the distance between the irradiation subject and the scanning electromagnet in the beam axis direction of a charged particle beam can be changed, and it is made possible to perform the combination of a plurality of parameters in particle beam irradiation, such as the combination of irradiation fields and irradiation position accuracies; thus, diverse irradiation variations can be set.

The particle beam therapy system 51 according to Embodiment 1 is provided with the beam generation apparatus 52 that generates the charged particle beam 3 and accelerates it by means of the accelerator 54; the beam transport system 59 that transports the charged particle beam 3 accelerated by the accelerator 54; and the particle beam irradiation apparatus 58 that irradiates the charged particle beam 3 transported by the beam transport system 59 onto the irradiation subject 11. The particle beam irradiation apparatus 58 is provided with the scanning electromagnets 1 and 2 that scans the charged particle beam 3 and the scanning electromagnet moving apparatus 4 that moves the scanning electromagnets 1 and 2 in such a way as to change the distance, in the beam axis direction of the charged particle beam 3, between the scanning electromagnets 1 and 2 and the irradiation subject 11. As a result, the distance between the irradiation subject and the scanning electromagnet in the beam axis direction of a charged particle beam can be changed, it is made possible to perform the combination of a plurality of parameters in particle beam irradiation, such as the combination of irradiation fields and irradiation position accuracies, and selection from diverse irradiation variations can be performed; therefore, an appropriate particle beam therapy can be performed.

Embodiment 2

In the case of Embodiment 1, it is conceivable that when at least one of the X-direction scanning electromagnet 1 and the Y-direction scanning electromagnet 2 is moved, the charged particle beam 3, which is swung at the maximum swing angle of the upstream scanning electromagnet 1, interferes with the magnetic pole of the downstream scanning electromagnet 2. In the case of Embodiment 2, a magnetic pole moving apparatus 29 is provided for the purpose of preventing the charged particle beam 3, which is swung at the maximum swing angle of the upstream scanning electromagnet 1, from interfering with the magnetic pole of the downstream scanning electromagnet 2, even when at least one of the X-direction scanning electromagnet 1 and the Y-direction scanning electromagnet 2 is moved. An irradiation apparatus according to Embodiment 2 differs from an irradiation apparatus according to Embodiment 1 in that the magnetic pole moving apparatus 29 is provided at least in the downstream Y-direction scanning electromagnet 2.

Figure 7:
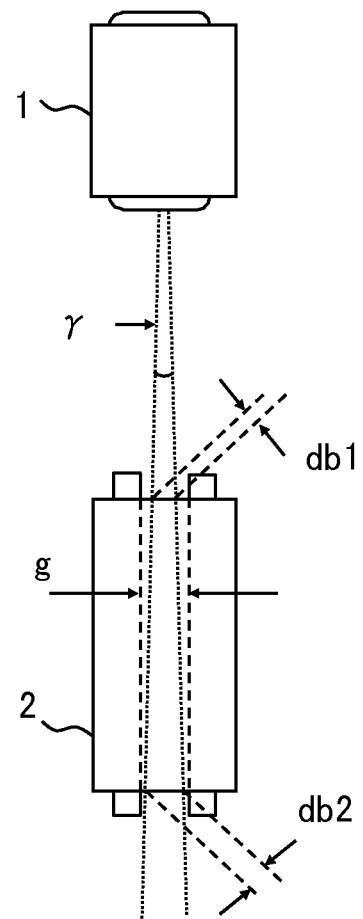
FIG. 7 is a diagram for explaining the relationship between the poles of a scanning electromagnet and a charged particle beam.

FIG. 7 is a diagram for explaining the relationship between the poles of a scanning electromagnet and a charged particle beam. The charged particle beam 3 is scanned by the upstream X-direction scanning electromagnet 1 at the swing angle γ in the X direction. In the downstream Y-direction scanning electromagnet 2, the charged particle beam 3 passes through the magnetic pole distance g of the Y-direction scanning electromagnet 2. The charged particle beam 3 passes through a top-end moving range db1 at the top end of the Y-direction scanning electromagnet 2, and passes through a bottom-end moving range db2 at the bottom end of the Y-direction scanning electromagnet 2. The bottom-end moving range db2 is wider than the top-end moving range db1; therefore, in order to prevent the charged particle beam 3 from interfering with the magnetic pole of the Y-direction scanning electromagnet 2, the magnetic pole distance g needs to be wider than the bottom-end moving range db2. In the case where the magnetic pole distance g is narrower than the bottom-end moving range db2, the charged particle beam 3 interferes with the magnetic pole of the Y-direction scanning electromagnet 2.

Figure 8:
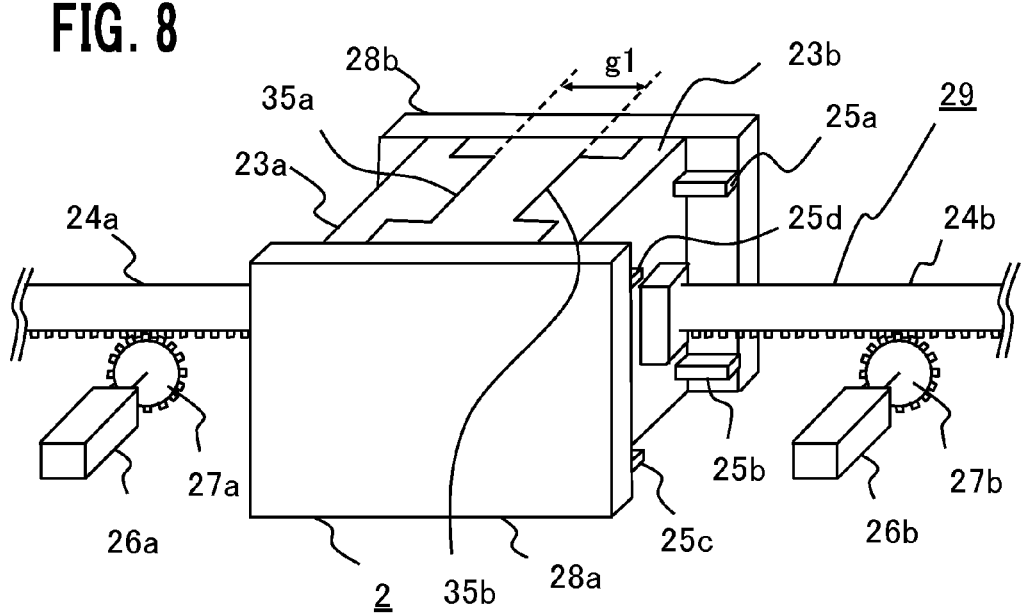
FIG. 8 is a configuration diagram illustrating a scanning electromagnet according to Embodiment 2 of the present invention.

FIG. 8 is a configuration diagram illustrating a scanning electromagnet according to Embodiment 2 of the present invention. FIG. 8 illustrates an example of the Y-direction scanning electromagnet 2 and the magnetic pole moving apparatus 29. The Y-direction scanning electromagnet 2 has two fixed yokes 28a and 28b and two moving iron cores 23a and 23b. The fixed yoke 28a is provided with moving guides 25c and 25d, and the fixed yoke 28b is provided with moving guides 25a and 25b; the moving iron cores 23a and 23b are moved by the magnetic pole moving apparatus 29 while being supported by the moving guides 25a, 25b, 25c, and 25d. The magnetic pole moving apparatus 29 includes two moving units that each move the two moving iron cores 23a and 23b. The moving unit has a pinion 27a (27b), a motor 26a (26b), and a rack 24a (24b). The rack 24a is mounted on the moving iron core 23a; the rack 24b is mounted on the moving iron core 23b. Rotation of the pinion 27a mounted on the motor 26a makes the rack 24a move; similarly, rotation of the pinion 27b mounted on the motor 26b makes the rack 24b move.

Figure 9:
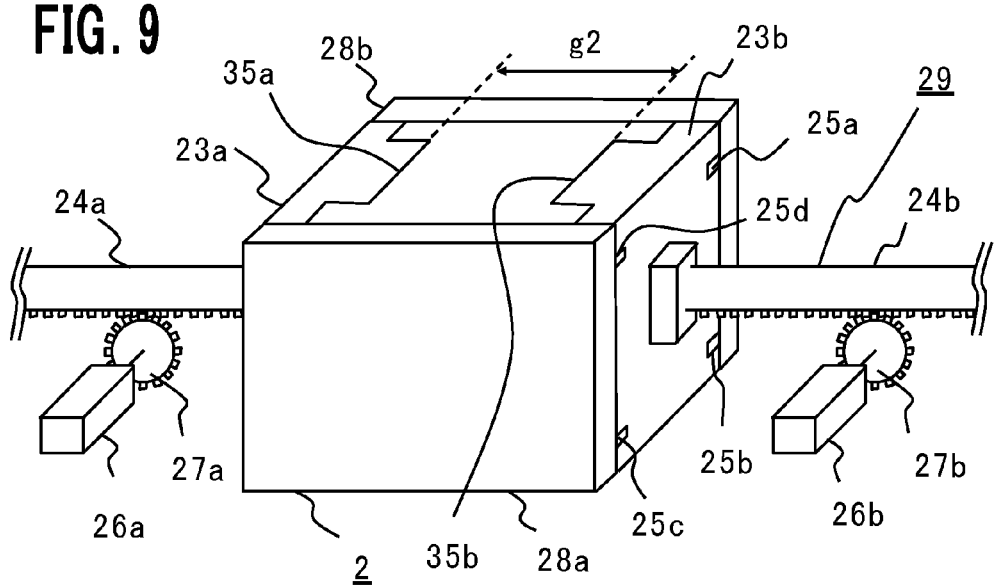
FIG. 9 is an example where the magnetic pole distance in the scanning electromagnet in FIG. 8 is set to be maximum.

FIG. 8 illustrates a case where the magnetic pole distance between the moving iron core 23a and the moving iron core 23b is g1. The coils of the Y-direction scanning electromagnet 2 are provided around the respective protrusion portions 35a and 35b of the moving iron cores 23a and 23b. The coil provided around the moving iron core 23a moves along with the moving iron core 23a; the coil provided around the moving iron core 23b moves along with the moving iron core 23b. FIG. 9 illustrates an example where the magnetic pole distance in the scanning electromagnet is set to be maximum. In FIG. 9, the moving iron cores 23a and 23b have moved up to their maximum limits; the magnetic pole distance between the moving iron core 23a and the moving iron core 23b is g2. In addition, g1<g2.

In the particle beam irradiation apparatus 58 according to Embodiment 2, the magnetic pole moving apparatus 29 is provided at least in the downstream Y-direction scanning electromagnet 2 and hence the magnetic pole distance g of the downstream Y-direction scanning electromagnet 2 can be changed; therefore, even in the case where at least one of the X-direction scanning electromagnet 1 and the Y-direction scanning electromagnet 2 is moved, the charged particle beam 3 can be prevented from interfering with the magnet poles of the downstream scanning electromagnet 2. Accordingly, in the case of the particle beam irradiation apparatus 58 according to Embodiment 2, the maximum irradiation field and the irradiation position accuracy suitable for the irradiation subject 11 can be selected in one of the X direction and the Y direction. Because the maximum irradiation field and the irradiation position accuracy can be selected in each of the X direction and the Y direction, diverse irradiation variations can be set in comparison with Embodiment 1.

Embodiment 3

Figure 10:
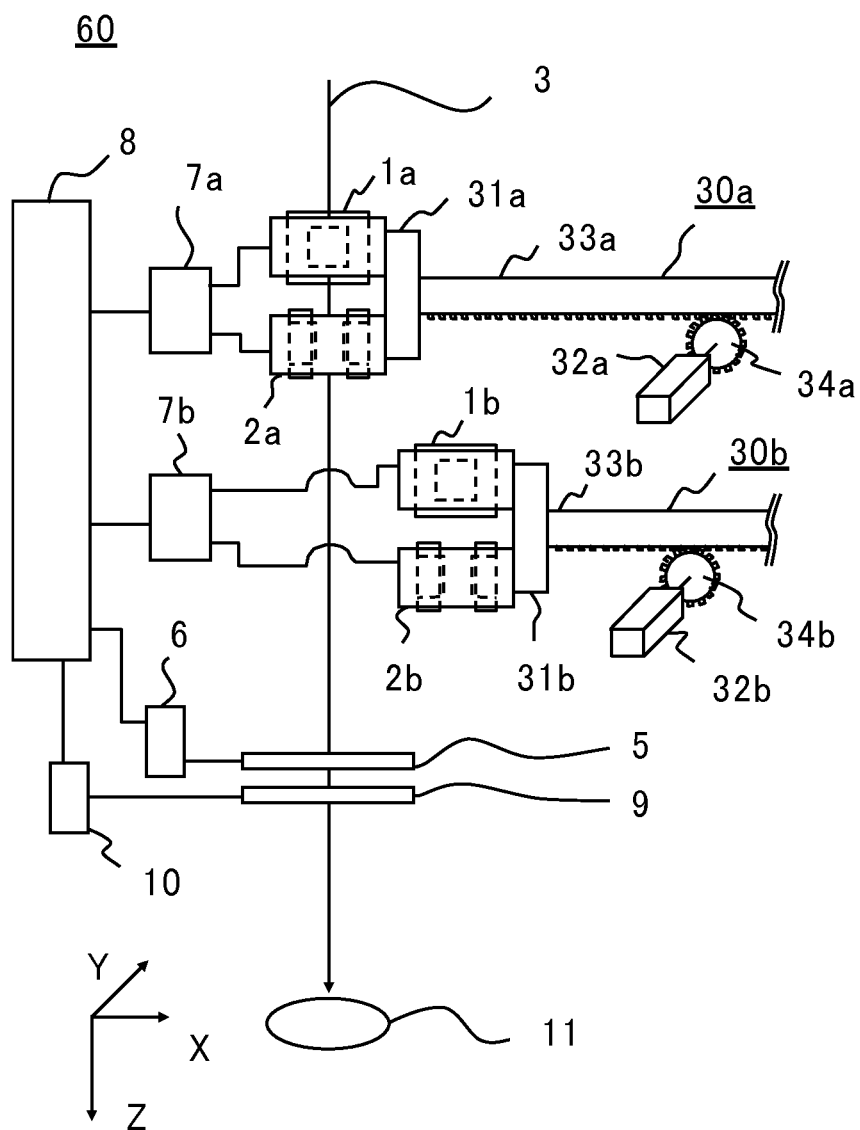
FIG. 10 is a configuration diagram illustrating a particle beam irradiation apparatus according to Embodiment 3 of the present invention.

FIG. 10 is a configuration diagram illustrating a particle beam irradiation apparatus according to Embodiment 3 of the present invention. A particle beam irradiation apparatus 60 according to embodiment 3 is an example where the distance between the X-direction scanning electromagnet 1/the Y-direction scanning electromagnet 2 and the irradiation subject 11 is discretely changed. FIG. 10 illustrates an example where there exist two pairs of X-direction scanning electromagnet and Y-direction scanning electromagnet. The particle beam irradiation apparatus 60 differs from the particle beam irradiation apparatus 58 according to Embodiment 1 in that an X-direction scanning electromagnet 1a and a Y-direction scanning electromagnet 2a, an X-direction scanning electromagnet 1b and a Y-direction scanning electromagnet 2b, two scanning electromagnet power sources 7a and 7b, and two scanning electromagnet moving apparatuses 30a and 30b are included therein.

The scanning electromagnet moving apparatus 30a has a fixation plate 31a on which the X-direction scanning electromagnet 1a and the Y-direction scanning electromagnet 2a are fixed, a rack 33a connected with the fixation plate 31a, a motor 32a, and a pinion 34a. The scanning electromagnet moving apparatus 30b has a fixation plate 31b on which the X-direction scanning electromagnet 1b and the Y-direction scanning electromagnet 2b are fixed, a rack 33b connected with the fixation plate 31b, a motor 32b, and a pinion 34b. Rotation of the pinion 34a mounted on the motor 32a makes the rack 33a move; similarly, rotation of the pinion 34b mounted on the motor 32b makes the rack 33b move. The scanning electromagnet moving apparatuses 30a and 30b each move the scanning electromagnets from a position where the charged particle beam 3 is scanned to a position where the charged particle beam 3 is not scanned.

In Embodiment 3, the distance between the X-direction scanning electromagnet 1/the Y-direction scanning electromagnet 2 and the irradiation subject 11 is discretely changed by the scanning electromagnet moving apparatus 30a and 30b; thus, it is only necessary to prepare the control input generation units corresponding to the number of discrete changes. In the particle beam irradiation apparatus 60 according to Embodiment 3, fewer control input generation units are utilized in comparison with the particle beam irradiation apparatus 58 according to Embodiment 1; thus, the work for preparing the control input generation units can be reduced, whereby the time prior to the start of actual operation of the particle beam irradiation apparatus can be shortened. The diversity of the particle beam irradiation apparatus 60 according to Embodiment 3 is less than the particle beam irradiation apparatus 58 according to embodiment 1; however, unlike conventional apparatuses, the particle beam irradiation apparatus 60 according to Embodiment 3 makes possible to perform the combination of two or more parameters in particle beam irradiation, such as the combination of the irradiation field and the irradiation position accuracy, can be performed, whereby diverse irradiation variations can be set.

As an example, there has been explained the spot scanning method; however, the present invention can also be applied to the raster scanning method.

The present invention can also be applied to a broad-irradiation Wobbler electromagnet. By utilizing the scanning electromagnet moving apparatus 4 and the scanning electromagnet moving apparatus 30 in the broad irradiation method so as to change the distance between the irradiation subject 11 and the Wobbler electromagnet, the irradiation field can be enlarged. In the scanning irradiation method, by making changeable the combination of the irradiation field and the irradiation position accuracy, as the combination of two or more parameters in particle beam irradiation, diverse irradiation variations can be implemented; in contrast, in the broad irradiation method, by making changeable the combination of the irradiation field and the beam flatness, as the combination of two or more parameters in particle beam irradiation, diverse irradiation variations can be implemented.

DESCRIPTION OF REFERENCE NUMERALS

1, 1a, 1b: X-direction scanning electromagnet
2, 2a, 2b: Y-direction scanning electromagnet
3: charged particle beam
4: scanning electromagnet moving apparatus
8: irradiation control apparatus
11: irradiation subject
23a, 23b: moving iron core
29: magnetic pole moving apparatus
30a, 30b: scanning electromagnet moving apparatus
51: particle beam therapy system
52: beam generation apparatus
54: synchrotron
58, 58a, 58b: particle beam irradiation apparatus
59: beam transport system
60, 60a, 60b: particle beam irradiation apparatus

The invention claimed is:

1. A particle beam irradiation apparatus that irradiates a charged particle beam accelerated by an accelerator onto an irradiation subject, the particle beam irradiation apparatus comprising:
    a scanning electromagnet that scans the charged particle beam in an X direction and a Y direction that are perpendicular to a beam axis; and
    a scanning electromagnet moving apparatus that moves the scanning electromagnet in such a way as to change the distance between the scanning electromagnet and the irradiation subject in the beam axis direction of the charged particle beam.

2. The particle beam irradiation apparatus according to claim 1, further including an irradiation control apparatus that controls the scanning electromagnet, based on desired irradiation position coordinates of the charged particle beam, wherein the irradiation control apparatus generates control inputs for controlling the scanning electromagnet, based on the distance between the scanning electromagnet and the irradiation subject.

3. The particle beam irradiation apparatus according to claim 2, wherein the irradiation control apparatus has a control input generation unit that generates control inputs based on the distance between the scanning electromagnet and the irradiation subject.

4. The particle beam irradiation apparatus according to claim 3, wherein the irradiation control apparatus has a plurality of control input generation units having different irradiation position accuracies based on the respective distances between the scanning electromagnet and the irradiation subject.

5. The particle beam irradiation apparatus according to claim 4, wherein the control input generation unit is a conversion table in which the control input is related to the desired irradiation position coordinates corresponding to the control input.

6. The particle beam irradiation apparatus according to claim 4, wherein the control input generation unit is a polynomial expression in which the control input is related to the desired irradiation position coordinates.

7. The particle beam irradiation apparatus according to claim 4,
wherein the scanning electromagnet includes a first scanning electromagnet that scans the charged particle beam in the X and Y directions and a second scanning electromagnet that is disposed at the downstream side of the first scanning electromagnet and scans the charged particle beam in the X and Y directions;
wherein the scanning electromagnet moving apparatus includes a scanning electromagnet moving apparatus that moves the first scanning electromagnet from a position where the charged particle beam is scanned to a position where the charged particle beam is not scanned, and a scanning electromagnet moving apparatus that moves the second scanning electromagnet from a position where the charged particle beam is scanned to a position where the charged particle beam is not scanned; and
wherein the charged particle beam is scanned by one of the first scanning electromagnet and the second scanning electromagnet.

8. The particle beam irradiation apparatus according to claim 4,
wherein the scanning electromagnet includes an X-direction scanning electromagnet that scans the charged particle beam in the X direction, and a Y-direction scanning electromagnet that is disposed at the downstream side of the X-direction scanning electromagnet and scans the charged particle beam in the Y direction;
wherein the Y-direction scanning electromagnet has moving iron cores in which the distance between magnetic poles thereof is changeable; and
wherein there is provided a magnetic pole moving apparatus that moves the moving iron cores of the Y-direction scanning electromagnet.

9. The particle beam irradiation apparatus according to claim 3, wherein the control input generation unit is a conversion table in which the control input is related to the desired irradiation position coordinates corresponding to the control input.

10. The particle beam irradiation apparatus according to claim 3, wherein the control input generation unit is a polynomial expression in which the control input is related to the desired irradiation position coordinates.

11. The particle beam irradiation apparatus according to claim 3,
wherein the scanning electromagnet includes a first scanning electromagnet that scans the charged particle beam in the X and Y directions and a second scanning electromagnet that is disposed at the downstream side of the first scanning electromagnet and scans the charged particle beam in the X and Y directions;
wherein the scanning electromagnet moving apparatus includes a scanning electromagnet moving apparatus that moves the first scanning electromagnet from a position where the charged particle beam is scanned to a position where the charged particle beam is not scanned, and a scanning electromagnet moving apparatus that moves the second scanning electromagnet from a position where the charged particle beam is scanned to a position where the charged particle beam is not scanned; and
wherein the charged particle beam is scanned by one of the first scanning electromagnet and the second scanning electromagnet.

12. The particle beam irradiation apparatus according to claim 3,
wherein the scanning electromagnet includes an X-direction scanning electromagnet that scans the charged particle beam in the X direction, and a Y-direction scanning electromagnet that is disposed at the downstream side of the X-direction scanning electromagnet and scans the charged particle beam in the Y direction;
wherein the Y-direction scanning electromagnet has moving iron cores in which the distance between magnetic poles thereof is changeable; and
wherein there is provided a magnetic pole moving apparatus that moves the moving iron cores of the Y-direction scanning electromagnet.

13. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is the particle beam irradiation apparatus according to claim 3.

14. The particle beam irradiation apparatus according to claim 2,
wherein the scanning electromagnet includes a first scanning electromagnet that scans the charged particle beam in the X and Y directions and a second scanning electromagnet that is disposed at the downstream side of the first scanning electromagnet and scans the charged particle beam in the X and Y directions;
wherein the scanning electromagnet moving apparatus includes a scanning electromagnet moving apparatus that moves the first scanning electromagnet from a position where the charged particle beam is scanned to a position where the charged particle beam is not scanned, and a scanning electromagnet moving apparatus that moves the second scanning electromagnet from a position where the charged particle beam is scanned to a position where the charged particle beam is not scanned; and
wherein the charged particle beam is scanned by one of the first scanning electromagnet and the second scanning electromagnet.

15. The particle beam irradiation apparatus according to claim 2,
wherein the scanning electromagnet includes an X-direction scanning electromagnet that scans the charged particle beam in the X direction, and a Y-direction scanning electromagnet that is disposed at the downstream side of the X-direction scanning electromagnet and scans the charged particle beam in the Y direction;

wherein the Y-direction scanning electromagnet has moving iron cores in which the distance between magnetic poles thereof is changeable; and wherein there is provided a magnetic pole moving apparatus that moves the moving iron cores of the Y-direction scanning electromagnet.

16. A particle beam therapy system comprising:

a beam generation apparatus that generates a charged particle beam and accelerates the charged particle beam by means of an accelerator;

a beam transport system that transports the charged particle beam accelerated by the accelerator; and a particle beam irradiation apparatus that irradiates the charged particle beam transported by the beam transport system onto an irradiation subject, wherein the particle beam irradiation apparatus is the particle beam irradiation apparatus according to claim 2.

17. The particle beam irradiation apparatus according to claim 1, wherein the scanning electromagnet includes a first scanning electromagnet that scans the charged particle beam in the X and Y directions and a second scanning electromagnet that is disposed at the downstream side of the first scanning electromagnet and scans the charged particle beam in the X and Y directions;

wherein the scanning electromagnet moving apparatus includes a scanning electromagnet moving apparatus that moves the first scanning electromagnet from a position where the charged particle beam is scanned to a position where the charged particle beam is not scanned, and a scanning electromagnet moving apparatus that moves the second scanning electromagnet from a position where the charged particle beam is scanned to a position where the charged particle beam is not scanned; and wherein the charged particle beam is scanned by one of the first scanning electromagnet and the second scanning electromagnet.

18. The particle beam irradiation apparatus according to claim 17, wherein the first scanning electromagnet or the second scanning electromagnet includes an X-direction scanning electromagnet that scans the charged particle beam in the X direction, and a Y-direction scanning electromagnet that is disposed at the downstream side of the X-direction scanning electromagnet and scans the charged particle beam in the Y direction;

wherein the Y-direction scanning electromagnet has moving iron cores in which the distance between magnetic poles thereof is changeable; and wherein there is provided a magnetic pole moving apparatus that moves the moving iron cores of the Y-direction scanning electromagnet.

19. The particle beam irradiation apparatus according to claim 1, wherein the scanning electromagnet includes an X-direction scanning electromagnet that scans the charged particle beam in the X direction, and a Y-direction scanning electromagnet that is disposed at the downstream side of the X-direction scanning electromagnet and scans the charged particle beam in the Y direction;

wherein the Y-direction scanning electromagnet has moving iron cores in which the distance between magnetic poles thereof is changeable; and wherein there is provided a magnetic pole moving apparatus that moves the moving iron cores of the Y-direction scanning electromagnet.

20. A particle beam therapy system comprising:

a beam generation apparatus that generates a charged particle beam and accelerates the charged particle beam by means of an accelerator;

a beam transport system that transports the charged particle beam accelerated by the accelerator; and a particle beam irradiation apparatus that irradiates the charged particle beam transported by the beam transport system onto an irradiation subject, wherein the particle beam irradiation apparatus is the particle beam irradiation apparatus according to claim 1.

* * * * *